US012257586B2

(12) United States Patent
Kim et al.

(10) Patent No.: US 12,257,586 B2
(45) Date of Patent: Mar. 25, 2025

(54) POROUS PARTICLE COMPOSITE FOR PCR WITH HEAT DISSIPATION FUNCTION

(71) Applicant: KOREA INSTITUTE OF SCIENCE AND TECHNOLOGY, Seoul (KR)

(72) Inventors: Sang Kyung Kim, Seoul (KR); Bong Kyun Kim, Seoul (KR); Jung Min Kim, Seoul (KR); Seungwon Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 924 days.

(21) Appl. No.: 17/055,167

(22) PCT Filed: May 14, 2019

(86) PCT No.: PCT/KR2019/005796
§ 371 (c)(1),
(2) Date: Nov. 13, 2020

(87) PCT Pub. No.: WO2019/221489
PCT Pub. Date: Nov. 21, 2019

(65) Prior Publication Data
US 2021/0197201 A1    Jul. 1, 2021

(30) Foreign Application Priority Data
May 15, 2018    (KR) .................... 10-2018-0055629

(51) Int. Cl.
*C12Q 1/68*    (2018.01)
*B01L 7/00*    (2006.01)
*C09K 5/14*    (2006.01)
*C12Q 1/686*    (2018.01)

(52) U.S. Cl.
CPC .............. *B01L 7/00* (2013.01); *C09K 5/14* (2013.01); *C12Q 1/686* (2013.01); *B01L 2300/0816* (2013.01); *B01L 2300/1861* (2013.01)

(58) Field of Classification Search
CPC .................................................... C09K 5/14
See application file for complete search history.

(56) References Cited

U.S. PATENT DOCUMENTS

| | | | | |
|---|---|---|---|---|
| 9,089,512 | B2 * | 7/2015 | Mooney | A61K 9/0024 |
| 10,519,490 | B2 * | 12/2019 | Kim | C12Q 1/6853 |
| 10,648,024 | B2 * | 5/2020 | Kim | B01L 3/50851 |
| 2006/0263799 | A1 | 11/2006 | Dertinger et al. | |
| 2013/0149746 | A1 | 6/2013 | Park | |
| 2014/0170664 | A1 * | 6/2014 | Roche | C12N 15/1006 |
| | | | | 435/270 |
| 2015/0056260 | A1 * | 2/2015 | Verma | C02F 1/505 |
| | | | | 427/217 |
| 2016/0265028 | A1 * | 9/2016 | Kim | B01L 3/50851 |
| 2017/0321265 | A1 * | 11/2017 | Kim | C12Q 1/6853 |

FOREIGN PATENT DOCUMENTS

| | | |
|---|---|---|
| EP | 2615171 A1 | 7/2013 |
| EP | 3064568 A1 | 9/2016 |
| KR | 10-2007-0075742 A | 7/2007 |
| KR | 1020130065319 A | 6/2013 |
| KR | 10-2013-0099092 A | 9/2013 |
| KR | 10-2015-0048964 A | 5/2015 |
| KR | 10-1670232 B1 | 10/2016 |
| KR | 101717966 B1 | 3/2017 |
| KR | 1020170106995 A | 9/2017 |
| KR | 1020170124891 A | 11/2017 |
| WO | 2016/115542 A1 | 7/2016 |

OTHER PUBLICATIONS

Choi et al, Mar. 15, 2018. Hydrogel micropost-based qPCR for multiplex detection of miRNAs associated with Alzheimer's disease. Biosensors and Bioelectronics, 101, pp. 235-244. (Year: 2018).*
Ekici et al., 2008. Thermal analysis of gold nanorods heated with femtosecond laser pulses. Journal of physics D: Applied physics, 41(18), 185501, pp. 1-11. (Year: 2008).*
Geng et al., 2015. Minimizing inhibition of PCR-STR typing using digital agarose droplet microfluidics. Forensic Science International: Genetics, 14, pp. 203-209. (Year: 2015).*
Kim et al., 2017. Gold nanorod-based photo-PCR system for one-step, rapid detection of bacteria. Nanotheranostics, 1(2), p. 178-184. (Year: 2017).*
Okumura et al., 2005. Point mutation detection with the sandwich method employing hydrogel nanospheres by the surface plasmon resonance imaging technique. Analytical Biochemistry, 339(2), pp. 328-337. (Year: 2005).*
Zhu, Z. and Yang, C.J., 2017. Hydrogel droplet microfluidics for high-throughput single molecule/cell analysis. Accounts of chemical research, 50(1), pp. 22-31. (Year: 2016).*
Choi et al., 2012. Multiplexed detection of mRNA using porosity-tuned hydrogel microparticles. Analytical chemistry, 84(21), pp. 9370-9378. (Year: 2012).*
Jung et al., Mar. 11, 2016. Extensible multiplex real-time PCR of MicroRNA using Microparticles. Scientific reports, 6(1), 22975, pp. 1-7. (Year: 2016).*
Jung et al., Epub Mar. 1, 2017. Extensible multiplex real-time PCR for rapid bacterial identification with carbon nanotube composite microparticles. Biosensors and Bioelectronics, 94, pp. 256-262. (Year: 2017).*

(Continued)

Primary Examiner — Stephanie K Mummert
Assistant Examiner — Olayinka A Oyeyemi
(74) Attorney, Agent, or Firm — Rabin & Berdo, P.C.

(57) ABSTRACT

The present invention relates to a porous particle composite for PCR, wherein the porous particle composite distributes photothermal nano-elements that generate heat by absorbing light in porous particles in which nucleic acid amplification occurs through temperature control so as not to adjust the temperature of the entire sample by using a hot plate or the like but to adjust the temperature inside the particles by irradiating light to the porous particles to allow nucleic acid amplification inside thereof, thereby reducing energy consumption and shortening diagnostic time.

13 Claims, 5 Drawing Sheets

Specification includes a Sequence Listing.

(56) References Cited

OTHER PUBLICATIONS

Kim et al., Jan. 2, 2018. Multiplex real-time PCR using temperature sensitive primer-supplying hydrogel particles and its application for malaria species identification. Plos one, 13(1), e0190451, pp. 1-12. (Year: 2018).*
Kim et al., 2022. Ultrafast real-time pcr in photothermal microparticles. ACS nano, 16(12), pp. 20533-20544. (Year: 2022).*
Mackey et al., 2014. The most effective gold nanorod size for plasmonic photothermal therapy: theory and in vitro experiments. The Journal of Physical Chemistry B, 118(5), pp. 1319-1326. (Year: 2014).*
Shen et al., 2009. NanoPCR observation: different levels of DNA replication fidelity in nanoparticle-enhanced polymerase chain reactions. Nanotechnology, 20(45), 455103, pp. 1-8. (Year: 2009).*
Yata et al., 2017. DNA nanotechnology-based composite-type gold nanoparticle-immunostimulatory DNA hydrogel for tumor photothermal immunotherapy. Biomaterials, 146, pp. 136-145. (Year: 2017).*
Jinjoo Kim et al., "Gold Nanorod-based Photo-PCR System for One-Step, Rapid Detection of Bacteria", Nanotheranostics, vol. 1, No. 2, pp. 178-185, May 6, 2017.
Jun Ho Son et al., "Rapid Optical Cavity PCR", Advanced Healthcare Materials, vol. 5, pp. 167-174, 2016.
Jun Ho Son et al., "Ultrafast photonic PCR", Light: Science & Applications, vol. 4, No. e280, pp. 1-7, Jul. 31, 2015.
Jung-Hoon Lee et al., "Plasmonic Photothermal Gold Bipyramid Nanoreactors for Ultrafast Real-Time Bioassays", Journal of the American Chemical Society, vol. 139, pp. 8054-8057, May 1, 2017.
Philip J. R. Roche et al., "Demonstration of a plasmonic thermocycler for the amplification of human androgen receptor DNA", Analyst, vol. 137, pp. 4475-4481, Jul. 17, 2012.

* cited by examiner

POROUS PARTICLE COMPOSITE FOR PCR WITH HEAT DISSIPATION FUNCTION

TECHNICAL FIELD

The present disclosure relates to a porous particle composite for PCR, wherein the porous particle composite distributes photothermal nanoelements that generate heat by absorbing light in porous particles in which nucleic acid amplification occurs through temperature control so as not to adjust the temperature of the entire sample by using a hot plate, etc. but to adjust the temperature inside the particles by irradiating light to the porous particles to allow nucleic acid amplification inside thereof, thereby reducing energy consumption and shortening diagnostic time.

BACKGROUND ART

Polymerase chain reaction (PCR) is a method of amplifying a specific genetic material desired to be detected, and is widely used to diagnose hereditary diseases by amplifying human DNA or diagnose infectious diseases by detecting the DNA of bacteria, viruses or fungi. However, with the existing polymerase chain reaction technology, it is difficult to analyze several nucleic acids quickly at the same time. Therefore, a technology of analyzing several nucleic acids simultaneously in real time using porous particles is being developed as in the following patent document.

PATENT DOCUMENT

Korean Patent No. 10-1670232 (registered on Oct. 24, 2016) "Porous structure and method for producing same".

In the PCR amplification using porous particles, nucleic acid amplifications in the particles through temperature cycling of 95° C. and about 50-60° C. The existing heating system requires temperature control for the entire liquid (water or oil) inside a PCR chip or channel comprising the porous particles. Because the temperature of the liquid outside the porous particles, which does not participate in the nucleic acid amplification, has to be adjusted, unnecessary energy consumption cannot be avoided and a lot of time is taken for the nucleic acid amplification.

DISCLOSURE

Technical Problem

The present disclosure is directed to providing a porous particle composite for PCR with heat dissipation function, which distributes photothermal nanoelements that generate heat by absorbing light in porous particles in which nucleic acid amplification occurs through temperature control so as not to adjust the temperature of the entire sample by using a hot plate, etc. but to adjust the temperature inside the particles by irradiating light to the porous particles to allow effective nucleic acid amplification inside thereof.

The present disclosure is also directed to providing a porous particle composite for PCR with heat dissipation function, which is capable of reducing energy consumption and shortening diagnostic time by adjusting the temperature inside porous particles rather than the entire sample.

The present disclosure is also directed to providing a porous particle composite for PCR with heat dissipation function, wherein one primer of a forward primer and a reverse primer is bound to the surface of photothermal nanoelements and the other primer is bound inside the porous particles and it is not necessary to provide primers separately to a PCR solution comprising the sample.

The present disclosure is also directed to providing a porous particle composite for PCR with heat dissipation function, wherein, since the one primer is detached from the surface of the photothermal nanoelements due to the heat applied to conduct PCR and participates in PCR, the decrease in PCR efficiency can be prevented although both primers are located inside the porous particles.

The present disclosure is also directed to providing a porous particle composite for PCR with heat dissipation function, wherein sonication is conducted for a predetermined time after the photothermal nanoelements are mixed with primers, so that the photothermal nanoelement and the primers are bound in such a manner that they can be separated by heat without using additional linkers.

Technical Solution

The present disclosure is embodied by the following exemplary embodiments in order to achieve the purpose described above.

According to an exemplary embodiment of the present disclosure, the porous particle composite for PCR according to the present disclosure comprises porous particles in which nucleic acid amplification occurs through temperature control and photothermal nanoelements that generate heat by absorbing light in the porous particles, wherein the temperature inside the porous particles can be adjusted to the temperature necessary for nucleic acid amplification by irradiating specific light to the porous particles.

According to another exemplary embodiment of the present disclosure, in the porous particle composite for PCR according to the present disclosure, the porous particle may be a hydrophilic polymer in solid state, having a porosity of 10-95 vol % based on total volume and a particle diameter of 10 μm to 1 mm.

According to another exemplary embodiment of the present disclosure, in the porous particle composite for PCR according to the present disclosure, the photothermal nanoelement may be any one or more selected from a group consisting of a metal nanoparticle, a carbon nanoelement, an inorganic nanoelement, an organic nanoelement, a quantum dot and a rare-earth element.

According to another exemplary embodiment of the present disclosure, in the porous particle composite for PCR according to the present disclosure, the photothermal nanoelement may have a diameter or length of 1-500 nm.

According to another exemplary embodiment of the present disclosure, in the porous particle composite for PCR according to the present disclosure, the photothermal nanoelements may be present in an amount of 0.01-50 mg per 1 mL of the porous particles.

According to another exemplary embodiment of the present disclosure, in the porous particle composite for PCR according to the present disclosure, the photothermal nanoelements may be fixed to the porous particles physically or chemically.

According to another exemplary embodiment of the present disclosure, in the porous particle composite for PCR according to the present disclosure, one primer of a forward primer and a reverse primer may be fixed inside the porous particles, the other primer may be attached to the surface of the photothermal nanoelements fixed inside the porous particles, and the other primer may be detached from the photothermal nanoelements due to heat generated in the photothermal nanoelements when light is irradiated to the porous particle composite for PCR.

According to another exemplary embodiment of the present disclosure, a method for preparing a porous particle composite for PCR according to the present disclosure comprises: a binding step of, by mixing one primer of a forward primer and a reverse primer in a solution wherein photothermal nanoelements are dispersed, binding the one primer onto the surface of the photothermal nanoelements; a first mixing step of forming a first mixture solution by mixing the photothermal nanoelements with the one primer bound and a porous particle-forming polymer solution; a second mixing step of forming a second mixture solution by mixing the first mixture solution with the other primer; and a curing step of preparing a porous particle composite having porosity, having the other primer of target nucleic acids fixed to inner pores and having the photothermal nanoelements with the one primer attached fixed to the inner pores by curing the second mixture solution.

According to another exemplary embodiment of the present disclosure, in the method for preparing a porous particle composite for PCR according to the present disclosure, the binding step may be performed by mixing one primer of a forward primer and a reverse primer in a solution wherein photothermal nanoelements are dispersed and conducting sonication for 30-60 minutes.

According to another exemplary embodiment of the present disclosure, a nucleic acid amplification device according to the present disclosure comprises a PCR chip comprising a porous particle composite which amplifies target nucleic acids by polymerase chain reaction inside thereof, a light irradiation unit which irradiates light to the porous particle composite and a controller which adjusts the light irradiated by the light irradiation unit such that the porous particle composite has a temperature where polymerase chain reaction occurs, wherein the porous particle composite is the porous particle composite described in claim 1.

According to another exemplary embodiment of the present disclosure, in the nucleic acid amplification device according to the present disclosure, the intensity of the light irradiated by the light irradiation unit may be controlled by controlling any one or more of the current, voltage, duty cycle and frequency of power applied to the light irradiation unit.

According to another exemplary embodiment of the present disclosure, in the nucleic acid amplification device according to the present disclosure, the controller may comprise alight setting unit which sets the condition of the light irradiated by the light irradiation unit such that the porous particle composite has a temperature where polymerase chain reaction occurs.

According to another exemplary embodiment of the present disclosure, the nucleic acid amplification device according to the present disclosure may further comprise a measurement unit which measures the porous particle composite located in the PCR chip to which light has been irradiated by the light irradiation unit and the controller may comprise a result analysis unit which determines the presence or amount of target nucleic acids by analyzing the result measured by the measurement unit.

According to another exemplary embodiment of the present disclosure, a nucleic acid amplification method nucleic acid amplification method according to the present disclosure comprises a sample reaction step of reacting a porous particle composite which amplifies target nucleic acids by polymerase chain reaction inside thereof with a sample, a light irradiation step of irradiating light to the porous particle composite which has reacted with the sample such that the porous particle composite has a temperature where polymerase chain reaction occurs after the sample reaction step, a measurement step of measuring the change of the porous particle composite after the light irradiation step and an analysis step of determining the presence or amount of target nucleic acids by analyzing the result measured in the measurement step, wherein the porous particle composite is the porous particle composite described above.

Advantageous Effects

The present disclosure may provide the following advantageous effects.

In the present disclosure, a porous particle composite distributes photothermal nanoelements that generate heat by absorbing light in porous particles in which nucleic acid amplification occurs through temperature control so as not to adjust the temperature of the entire sample by using a hot plate or the like but to adjust the temperature inside the particles by irradiating light to the porous particles to allow effective nucleic acid amplification inside thereof.

In addition, the present disclosure is capable of reducing energy consumption and shortening diagnostic time by adjusting the temperature inside porous particles rather than the entire sample.

In addition, the present disclosure provides an effect that it is not necessary to provide primers separately to a PCR solution comprising a sample since one primer of a forward primer and a reverse primer is bound to the surface of photothermal nanoelements and the other primer is bound inside the porous particles.

In addition, the present disclosure provides an effect that since the one primer is detached from the surface of the photothermal nanoelements due to the heat applied to conduct PCR and participates in PCR, the decrease in PCR efficiency can be prevented although both primers are located inside the porous particles.

In addition, the present disclosure provides an effect that sonication is conducted for a predetermined time after the photothermal nanoelements are mixed with primers, so that the photothermal nanoelement and the primers are bound in such a manner that they can be separated by heat without using additional linkers.

DETAILED DESCRIPTION OF MAIN ELEMENTS

Figure 1:
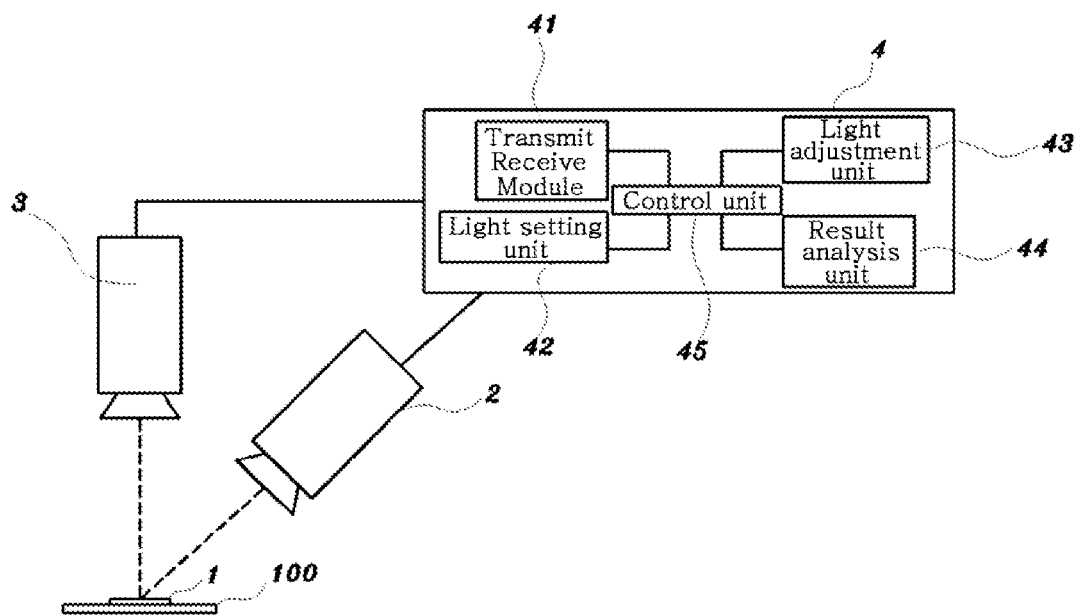
FIG. 1 schematically shows the configuration of a nucleic acid amplification device using a porous particle composite for PCR according to an exemplary embodiment of the present disclosure.

1: PCR chip
2: light irradiation unit
3: measurement unit
4: controller
41: transmit receive unit
42: light setting unit
43: light adjustment unit
44: result analysis unit
45: control unit

BEST MODE

Hereinafter, a porous particle composite for PCR according to the present disclosure with heat dissipation function and a device and a method for nucleic acid amplification using the same are described in detail referring to the attached drawings. Unless defined otherwise, all the terms used in this specification have the same meaning as would be generally understood by those of ordinary skill in the art to which the present disclosure belongs. If the general meaning is different to the meaning of the terms used in this specification, it is up to the definition of this specification. In addition, a detailed description of known functions and configurations is omitted to avoid making the subject matter of the present disclosure unnecessarily unclear. Throughout the specification, when it is described that a certain part "comprises" a certain component, this indicates that the part may further comprise another component instead of excluding another component unless specified otherwise.

A porous particle composite for PCR according to an exemplary embodiment of the present disclosure with heat dissipation function comprises porous particles in which nucleic acid amplification occurs through temperature control and photothermal nanoelements that generate heat by absorbing light in the porous particles, wherein the temperature inside the porous particles can be adjusted to the temperature necessary for nucleic acid amplification by irradiating specific light to the porous particles.

Nucleic acid amplification occurs inside the porous particles when temperature is adjusted. Various existing porous particles having porosity and nucleic acid amplification occurring inside thereof may be used. For example, the porous particles comprise pores and a forward primer and/or a reverse primer for polymerase chain reaction of target nucleic acids may be fixed physically or chemically inside the pores (both primers of target nucleic acids can be provided in liquid phase without being fixed inside the pores). The porous particles may have a porosity of 10-95 vol % based on total volume, may have any shape of spherical, disc and semi-spherical shapes, and may have a particle diameter of 10 μm to 1 mm. The porous particles may further comprise any one or more of an encoder providing the information of the primers fixed inside the pores, a fluorescence marker providing the quantitative information of the amplified nucleic acids and a probe emitting fluorescence. The porous structure may be prepared from a polymer (pre-polymer) that can be solidified. Examples may comprise any one or more polymer of polyethylene glycol diacrylate (PEG-DA), polyacrylamide (PA) and agarose. The fixation of the primer inside the pores may be achieved, for example, by chemically fixing the terminal acryl group of the primer to the porous particle. The primer may also be fixed inside the porous particles by a linker. The linker may have a length of 1-100 nm, and the linker may be one that can be cleaved by any one of heat, light and a chemical substance.

The photothermal nanoelements generate heat by absorbing light inside the porous particles. The photothermal nanoelement may be any one or more selected from a group consisting of a metal nanoparticle, a carbon nanoelement, an inorganic nanoelement, an organic nanoelement, a quantum dot and a rare-earth element.

The metal nanoparticle may be any one or more selected from a group consisting of gold, silver, platinum and palladium. The carbon nanoelement may be any one or more selected from a group consisting of graphene, graphene oxide (GO), carbon nanotube (CNT), CNT-COOH and reduced graphene oxide (rGO). The inorganic nanoelement may be any one or more selected from a group consisting of porous silicon, silicon oxide nanoparticle, bismuth sulfide nanorod, $FeSe_2$-decorated $Bi_2Se_3$ nanosheet, PEGylated $Cu_3BiS_3$ semiconductor nanorod and iron oxide-decorated $MoS_2$ nanosheet. The organic nanoelement may be any one or more selected from a group consisting of porphysome-based NPs, a core formed by a mixture of doxorubicin (DOX) and ICG surrounded by a poly-(lactic-co-glycolic acid) (PLGA)-lecithin-polyethylene shell, nanostructured porphyrin, indocyanine green (ICG), polyaniline, polypyrrole, poly[(diketopyrrolopyrrole-alt-cyclopentadithiophene)-ran-(diketopyrrolopyrrole-alt-thiadiazoloquinoxaline)] and PEDOT:PPS. The quantum dot may be any one or more selected from a group consisting of CuS, SuSe QDs, Ge-QDs and $MoO_3$-x quantum dots. And, the rare-earth element may be any one or more selected from a group consisting of $Yb^{3+}$—$Er^{3+}$-co-doped nanoparticles, $Nd^{3+}$ ion-doped nanocrystals, $Nd^{3+}$-doped $NaYF_4$ and neodymium (III)-doped fluoride nanoparticles. In addition, the photothermal nanoelements may have any one shape selected from sphere, rod, hexahedron, bipyramid, nanocage and nanostar and may have a diameter or length of 1-500 nm. Specifically, the photothermal nanoelements may be present in an amount of 0.01-50 mg per 1 mL of the porous particles and may be fixed to the porous particles physically or chemically. For example, the binding to the porous particles may be achieved by a linker having a functional group reacting with the photothermal nanoelements on one end and a functional group reacting with the porous particles (e.g., acryl group, thiol group, etc.) on the other end. One or more primer and/or probe may be fixed physically or chemically to the photothermal nanoelements distributed inside the porous particles. For example, the primer (or probe) may be linked by a linker, the linker may have a length of 1-100 nm, and the linker may be cleaved by any one of heat, light and a chemical substance.

A method for preparing a porous particle composite for PCR with heat dissipation function according to another exemplary embodiment of the present disclosure comprises a mixing step of forming a mixture solution by mixing a porous particle-forming polymer solution, photothermal nanoelements and primers of target nucleic acids and a curing step of preparing a porous particle composite having porosity, having the primers of target nucleic acids fixed to inner pores and having the photothermal nanoelements distributed inside by curing the mixture solution. The porous particle-forming polymer solution may contain a hydrophilic polymer for forming particles (e.g., PEG 700DA, etc.), a porogen (e.g., PEG 600, etc.), a photoinitiator (e.g., Darocur 1173, etc.), etc.

A method for preparing a porous particle composite for PCR with heat dissipation function according to another exemplary embodiment of the present disclosure comprises a binding step of, by mixing one primer of a forward primer and a reverse primer in a solution wherein photothermal nanoelements are dispersed and conducting sonication for 30-60 minutes, binding the one primer onto the surface of the photothermal nanoelements; a first mixing step of forming a first mixture solution by mixing the photothermal nanoelements with the one primer bound and a porous particle-forming polymer solution; a second mixing step of forming a second mixture solution by mixing the first mixture solution with the other primer; and a curing step of preparing a porous particle composite having porosity, having the other primer of target nucleic acids fixed to inner pores and having the photothermal nanoelements with the one primer attached fixed to the inner pores by curing the second mixture solution. When light is irradiated to the porous particle composite prepared by the above-described method for conducting PCR, the other primer remains fixed inside the porous particles but the one primer is detached from the surface of the photothermal nanoelements due to heat generated by the photothermal nanoelements. Through this, decreased PCR efficiency that may occur as both primers are present inside the porous particles may be prevented.

A nucleic acid amplification device using a porous particle composite for PCR with heat dissipation function according to another exemplary embodiment of the present disclosure will be described referring to FIG. 1. The nucleic acid amplification device comprises a PCR chip 1 comprising a porous particle composite which amplifies target nucleic acids by polymerase chain reaction inside thereof, a light irradiation unit 2 which irradiates light to the porous particle composite, a measurement unit 3 which measures the porous particle composite located in the PCR chip 1 to which light has been irradiated by the light irradiation unit 2, a controller 4 which adjusts the light irradiated by the light irradiation unit 2 such that the porous particle composite has a temperature where polymerase chain reaction occurs and determines the presence and/or amount of target nucleic acids by analyzing the result measured by the measurement unit 3, etc.

The PCR chip 1 comprises a porous particle composite which amplifies target nucleic acids by polymerase chain reaction inside thereof. When a sample is injected to the PCR chip and light is irradiated by the light irradiation unit 2 such that the porous particle composite has a temperature where polymerase chain reaction occurs, a target substance is amplified by polymerase chain reaction if the target substance is present in the sample. A detailed description of the porous particle composite will be omitted because it was described in detail above. The PCR chip 1 has a microchannel with, e.g., an inlet and an outlet, formed. A porous particle composite dispersed in a buffer is present in the microchannel, and the sample is injected into the microchannel for analysis.

The light irradiation unit 2 irradiates light to the PCR chip (specifically, to the porous particle composite) under control by the controller 4. When the light irradiation unit 2 irradiates light to the porous particle composite, photothermal nanoelements of the porous particle composite absorb the light and generate heat such that the porous particle composite has a temperature where polymerase chain reaction occurs. The light irradiation unit 2 may be, e.g., a laser or an LED and may irradiate light with a wavelength of 200-20000 nm. The intensity of the light irradiated by the light irradiation unit 2 may be adjusted (i.e., the temperature of the porous particle composite may be adjusted) by controlling the current, voltage, duty cycle, frequency, etc. of the power supplied to the light irradiation unit 2.

The measurement unit 3 measures the change of the porous particle composite located in the PCR chip 1 to which light has been irradiated by the light irradiation unit 2. When optimum light is irradiated directly to the PCR chip 1 to which a sample containing target nucleic acids has been injected, change occurs in the porous particle composite as the polymerase chain reaction occurs in the porous particle composite. The measurement unit 3 measures the change and transmits the result to the controller 4. The measurement unit 3 may be, e.g., a fluorescence microscope.

The controller 4 adjusts the light irradiated by the light irradiation unit 2 such that the porous particle composite has a temperature where polymerase chain reaction occurs and determines the presence and/or amount of target nucleic acids by analyzing the result measured by the measurement unit 3 and comprises a transmit receive module 41 which exchanges information with the light irradiation unit 2 and the measurement unit 3, a light setting unit 42 which sets the condition of the light irradiated by the light irradiation unit 2 such that the porous particle composite has a temperature where polymerase chain reaction occurs, a light adjustment unit 43 which controls the irradiated by the light irradiation unit 2 by adjusting power applied to the light irradiation unit 2 depending on the condition set by the light setting unit 42, a result analysis unit 44 which determines the presence and/or amount of target nucleic acids by analyzing the result measured by the measurement unit 3, a control unit 45 which controls the overall operation of the controller 4, etc.

The light setting unit 42 sets the condition of the light irradiated by the light irradiation unit 2 such that the porous particle composite has a temperature where polymerase chain reaction occurs. For example, after placing the PCR chip 1 with no sample injected on a support 100, the power applied to the light irradiation unit 2 is adjusted to change the light irradiated to the porous particle composite 1 by the light irradiation unit 2. Then, the temperature of the porous particle composite is measured using a temperature sensor (not shown), etc. and then analyzed.

The result analysis unit 44 determines the presence and/or amount of target nucleic acids by analyzing the result measured by the measurement unit 3. For example, the presence and/or amount of target nucleic acids may be determined by measuring fluorescence intensity from the result measured by the measurement unit (fluorescence microscope), and the result may be displayed on a display (not shown).

A nucleic acid amplification method using a porous particle composite for PCR with heat dissipation function according to another exemplary embodiment of the present disclosure comprises a sample reaction step of injecting a sample to a PCR chip 1 on which a porous particle composite which amplifies target nucleic acids by polymerase chain reaction inside thereof is located, a light irradiation step of irradiating light to the PCR chip 1 using a light irradiation unit 2 after the sample reaction step such that the porous particle composite has a temperature where polymerase chain reaction occurs, a measurement step of measuring the change of the porous particle composite located on the PCR chip 1 using a measurement unit 3 after the light irradiation step, and an analysis step of determining the presence and/or amount of target nucleic acids by analyzing the result measured in the measurement step.

Hereinafter, the present disclosure will be described in detail through examples. However, the following examples are for illustrative purposes only and the scope of the present disclosure is not limited by the examples.

<Example 1> Preparation of Porous Particle Composite for PCR

1. Porous Particle Composite for PCR 1

After mixing 40% of PEG (polyethylene glycol) 600, 20% of PEG 700DA, 35% of a gold nanoparticle solution (The gold nanoparticle solution was formed by concentrating Nanopartz's AC12-10-808-CTAB-DIH-100-1 2-fold. The concentration was performed by conducting centrifugation at 12000 rpm for 10 minutes, collecting the gold nanoparticles uniformly distributed in the solution to the bottom surface of the tube and removing half of the upper solution with a pipette.) and 5% (v/v) of Darocur 1173, vortexing and spinning down were performed. After mixing the solution with 10 μM β-actin forward primers

[5'-CCTGGCACCCAGCACAAT-3' (SEQ ID NO: 1)]

at 9:1 (v/v) and performing vortexing and spinning down, the solution was cured by irradiating UV. The cured particles were put in a DIT solution (DI water+Twin 20 (Twin 20 concentration: 0.05 wt %)). After performing vortexing and spinning down for 20 seconds and buffer-exchanging with a DIT solution, vortexing and spinning down were performed for 20 seconds for a total of 3 times. Then, a porous particle composite for PCR 1 dispersed in a DIT solution was prepared by buffer-exchanging with a fresh DIT solution.

2. Porous Particle Composite for PCR 2

(1) After mixing a carbon nanoelement solution (0.5 mg of rGO (rGO with a length of 5-7 μm) per 1 mL of DI water) and 200 μM β-actin reverse primers

[5'-GCCGATCCACACGGAGTACT-3' (SEQ ID NO: 2)]

at a volume ratio of 1:1, a mixture solution was obtained by conducing sonication for 30 minutes.

(2) After mixing 40% of PEG 600, 20% of PEG 700DA, 35% of the mixture solution and 5% (v/v) of Darocur 1173, a solution was prepared by performing vortexing and spinning down. After mixing the solution with 10 μM β-actin forward primers

[5'-CCTGGCACCCAGCACAAT-3' (SEQ ID NO: 1)]

at 9:1 (v/v) and performing vortexing and spinning down, the solution was cured by irradiating UV. The cured particles were put in a SC solution (DI water+sodium chlorate (sodium chlorate concentration: 0.2 wt %)). After performing vortexing and spinning down for seconds and buffer-exchanging with a SC solution, vortexing and spinning down were performed for 20 seconds for a total of 6 times. Then, a porous particle composite for PCR 2 dispersed in a SC solution was prepared by buffer-exchanging with a fresh SC solution.

3. Porous Particle Composite for PCR 3

A porous particle composite for PCR 3 dispersed in a SC solution was prepared in the same manner as in Example 1-2, except that CNT-COOH (having a length of 1 μm and a width of 1 nm) was used instead of rGO.

4. Porous Particle Composite for PCR 4

A porous particle composite for PCR 4 dispersed in a SC solution was prepared in the same manner as in Example 1-2, except that GO (having a length of 5-7 μm) was used instead of rGO.

<Example 2> Preparation of Porous Particles for PCR

Porous particles for PCR dispersed in DIT was prepared in the same manner as in Example 1-1, except that DI water was used instead of the gold nanoparticle solution.

<Example 3> Characterization of Porous Particle Composite for PCR

Figure 2:
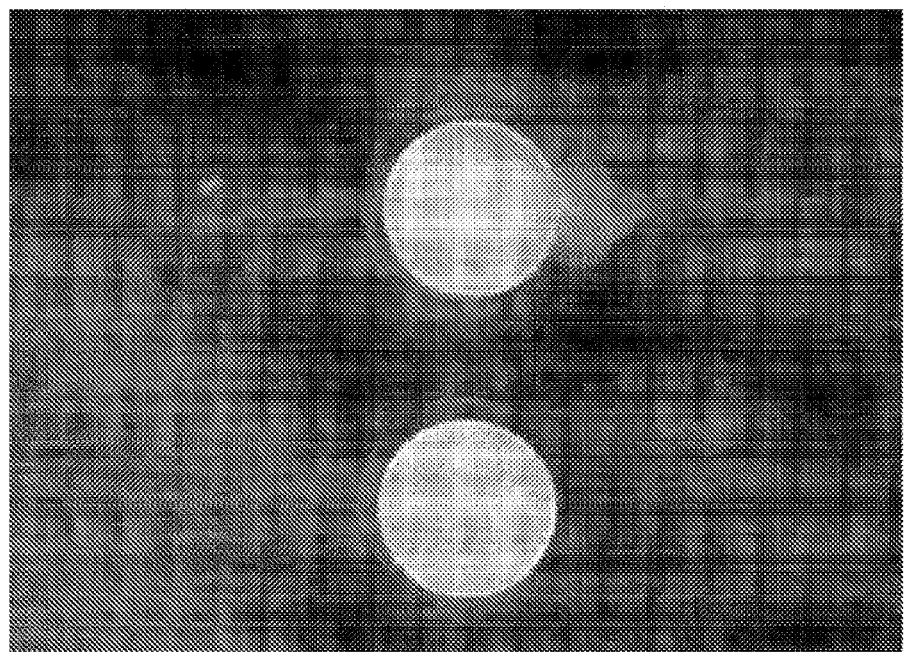
FIG. 2 is a fluorescence microscopic image of a porous particle composite for PCR according to an exemplary embodiment of the present disclosure.

1. The porous particle composite prepared in Example 1-1 and the porous particles prepared in Example 2 were stained with rhodamine B and observed with a fluorescence microscope (Zeiss Axionplan 2 imaging (LSM 5 PASCAI)). The result is shown in FIG. 2. In FIG. 2, the top image shows the porous particles and the bottom image shows the porous particle composite.

2. As seen from FIG. 2, black dots are observed on the porous particle composite, unlike the porous particles. This means that gold nanoparticles are dispersed uniformly on the porous particles.

<Example 4> Confirmation of Heat Dissipation Function of Porous Particle Composite for PCR 1. A PCR chip having a microchannel with an inlet and an outlet was formed by pouring a mixture solution of PDMS and a curing agent on a silicon wafer (mold) and curing the same.

2. A DIT solution in which the porous particle composite prepared in Example 1-1 was dispersed was injected into the microchannel through the inlet using a pipette. Then, after irradiating light from a light source 3 mm apart from the PCR chip, the temperature inside the porous particle composite was measured. The result is shown in Table 1. A 2-W, 800-nm laser (Changchun New Industries Optoelectronics Tech) was used as the light source and the measurement was made by adjusting duty, with the frequency of power supplied to the 2-W, 800-nm laser fixed to 1000 Hz.

TABLE 1

| Duty of supplied power | 10% | 20% | 40% | 60% |
|---|---|---|---|---|
| Temperature of porous particle composite (° C.) | 30 | 60 | 95 | 130 |

3. Also, porous particle composites for PCR dispersed in SC solutions were prepared under the same condition as in Example 1-2, except that 0.25, 0.125 or 0.0625 mg of rGO was used per 1 mL of DI water. The SC solution in which the porous particle composite for PCR was dispersed, prepared in Example 1-2 or Example 4-3, was injected into the microchannel through the inlet. Then, after irradiating light from a light source 1 cm apart from the PCR chip, the temperature inside the porous particle composite was measured. The result is shown in Table 2. A 2-W, 800-nm laser was used as the light source and the measurement was made at a duty of 100% with the frequency of power supplied to the 2-W, 800-nm laser fixed to 1000 Hz.

TABLE 2

| Porous particle composite | 0.5 mg/mL rGO | 0.25 mg/mL rGO | 0.125 mg/mL rGO | 0.0625 g/mL rGO |
|---|---|---|---|---|
| Temperature of porous particle composite (° C.) | 95 | 78 | 64 | 48 |

4. Also, each of the porous particle composites for PCR dispersed in SC solutions, prepared in Example 1-2 to 1-4, was injected into the microchannel through the inlet. Then, after irradiating light from a light source 3 mm apart from the PCR chip while gradually increasing the intensity of the light, the temperature inside the porous particle composite was measured. It was investigated whether the temperature inside the porous particle composite was increased depending on the increase of the light intensity and whether the porous particle composite had temperatures of 60 and 95° C. The result is shown in Table 3. A 2-W, 800-nm laser was used as the light source and the measurement was made while gradually increasing a duty from 0 to 100% with the frequency of power supplied to the 2-W, 800-nm laser fixed to 1000 Hz.

TABLE 3

|  | Example 1-2 | Example 1-3 | Example 1-4 |
|---|---|---|---|
| Whether temperature of porous particle composite increases | O | O | O |
| Whether porous particle composite has temperatures of 60 and 90° C. | O | O | O |

5. From Table 1, it can be seen that the temperature of the porous particle composite can be adjusted by adjusting the duty of power supplied to the light source. Therefore, it can be seen that the temperature of the porous particle composite can be adjusted to the temperature necessary for conducting PCR (roughly, denaturation is conducted at 95° C. and annealing is conducted at 60° C.). Also, from Table 2, it can be seen that the temperature of the porous particle composite can be adjusted to the temperature necessary for conducting PCR when carbon nanoelements are used instead of metal nanoparticles. In addition, it can be seen that the carbon nanoelements can induce photothermal reaction in the porous particle composite since the temperature of the porous particle composite is changed depending on the concentration of the carbon nanoelements. Also, from Table 3, it can be seen that the temperature of the porous particle composite can be adjusted to the temperature necessary for conducting PCR when various types of carbon nanoelements are used.

<Example 5> Confirmation of Nucleic Acid Amplification Using Porous Particle Composite for PCR 1. Nucleic Acid Amplification Using Porous Particle Composite Using Metal Nanoparticles (1) The porous particle composite prepared in Example 1-1, dispersed in a DIT solution, was injected into the microchannel of the PCR chip prepared in Example 4-1 using a pipette. Then, after injecting a PCR solution into the microchannel and waiting for 30 minutes, a PCR chip 1 was prepared by buffer-exchanging with mineral oil. The composition (v/v) of the PCR solution was: 5% of β-actin reverse primers

[5'-GCCGATCCACACGGAGTACT-3' (SEQ ID NO: 2)]

6.25% of templates (β-actin [5'-CCTGGCACCCAGCACAATGAAGATCAAGATCATTGC

TCCTCCTGAGCGCAAGTACTCCGTGTGGATCGGC-3' (SEQ ID NO: 3)]), 38.75% of DI water and 50% of SYBR 1 Mastermix (Nanobiosys).

Figure 3A:
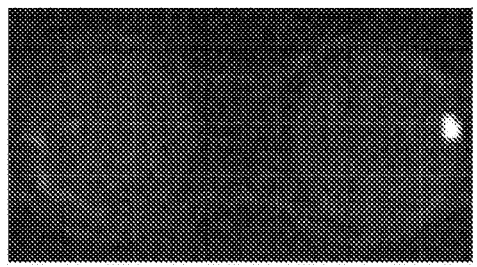
FIG. 3A to FIG. 3D show fluorescence microscopic images showing the result of nucleic acid amplification using a porous particle composite for PCR according to an exemplary embodiment of the present disclosure.
Figure 3B:
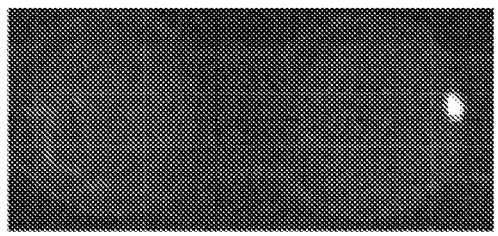
Figure 3C:
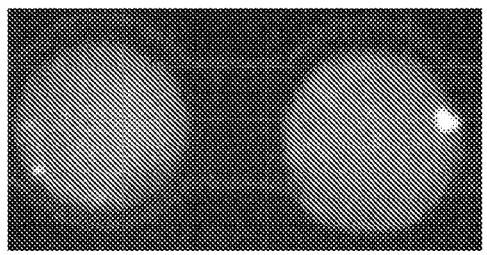
Figure 3D:
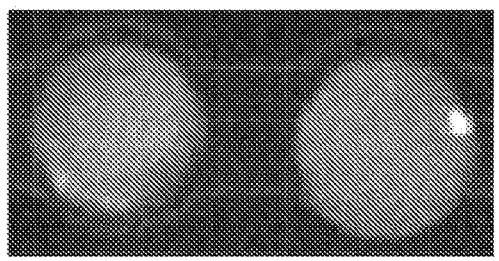
Figure 4:
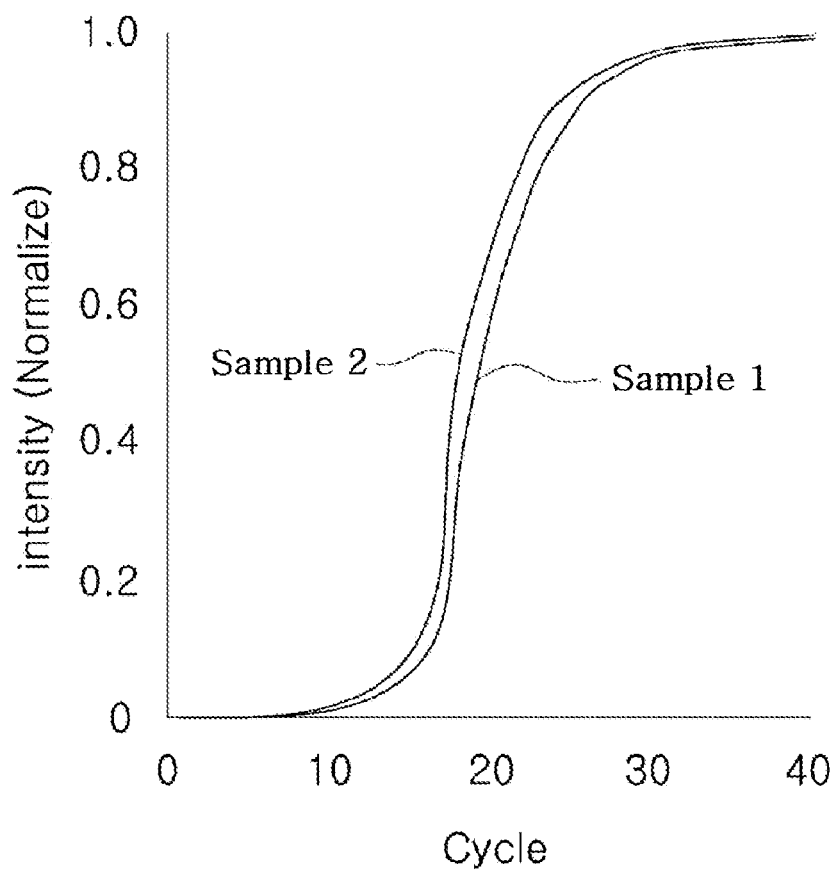
FIG. 4 shows a result of quantifying the result of nucleic acid amplification using a porous particle composite for PCR according to an exemplary embodiment of the present disclosure.

(2) After placing the PCR chip 1 on a fluorescence microscope (Zeiss Axionplan 2 imaging (LSM 5 PASCAI)), polymerase chain reaction was conducted according to the following temperature cycle by irradiating light from a light source (2-W, 800-nm laser) 3 mm apart from the PCR chip 1. Pre-denaturation was performed at 95° C. for 8 seconds, denaturation at 95° C. for 7 seconds, annealing at 60° C. for 15 seconds (for a total of 888 seconds). The temperature of the porous particle composite inside the PCR chip 1 could be adjusted to 60° C. and 95° C. by adjusting the duty of power supplied to the 2-W, 800-nm laser (As confirmed in Example 4, when the frequency was fixed to 1000 Hz, the temperature of the porous particle composite could be adjusted to 60° C. by adjusting the duty of the power to 20% and the temperature of the porous particle composite could be adjusted to 95° C. by adjusting the duty to 40%.). The polymerase chain reaction was conducted for a total of 40 cycle. After each cycle, the fluorescence image of the porous particle composite was acquired and the fluorescence intensity was quantified. FIG. 3A to FIG. 3D show fluorescence microscopic measurement results of the porous particle composites after specific cycles. FIG. 3A is the fluorescence image before cycling, FIG. 3B is the fluorescence image after 10 cycles, FIG. 3C is the fluorescence image after 25 cycles, and FIG. 3D is the fluorescence image after 40 cycles. FIG. 4 shows a result of quantifying the fluorescence intensity of the porous particle composites depending on cycles. In FIG. 4, sample 1 indicates the measurement result for the porous particle composite on the left sides in FIG. 3A to FIG. 3D, and sample 2 indicates the measurement result for the porous particle composite on the right sides in FIG. 3A to FIG. 3D.

Figure 5A:
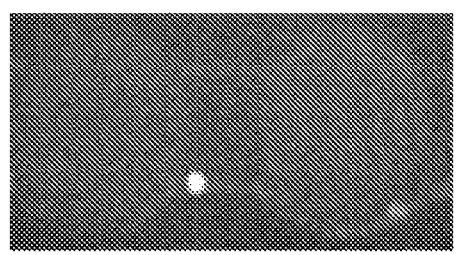
FIG. 5A and FIG. 5B show reference fluorescence microscopic images used to illustrate the nucleic acid amplification effect of a porous particle composite for PCR according to an exemplary embodiment of the present disclosure.
Figure 5B:
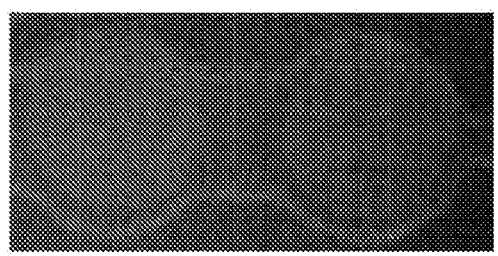

(3) FIG. 5A is a fluorescence image obtained after placing the PCR chip 1 on a fluorescence microscope and waiting for 888 seconds without irradiating light. After preparing a PCR chip 2 under the same condition as in Example 5-1 (1), except that a DIT solution in which the porous particles prepared in Example 2 were dispersed was used instead of the porous particle composite dispersed in a DIT solution, the PCR chip 2 was placed on a fluorescence microscope 3 mm apart from a light source. After irradiating light under the same condition as in Example 5-1 (1) (i.e., after 40 cycles), the fluorescence image of the porous particles was obtained as shown in FIG. 5B.

(4) From FIGS. 3A to 3D and 4, it can be seen that the fluorescence intensity becomes stronger with the progress of cycles. It can be seen that polymerase chain reaction can be conducted through self-heating of the porous particle composite without using a hot plate. From FIGS. 3A to 3D, 4, 5A and 5B, it can be seen that the fluorescence intensity of FIG. 5A and FIG. 5B is significantly lower than that of FIG. 3D.

Therefore, it can be seen that appropriate light was not irradiated to the porous particle composite or polymerase chain reaction did not occur even when light was irradiated to the porous particle. That is to say, it can be seen that polymerase chain reaction can be conducted effectively through self-heating if metal nanoparticles are distributed in the porous particles and appropriate light is irradiated.

2. Nucleic Acid Amplification Using Porous Particle Composite Using Carbon Nanoelements (1) The porous particle composite prepared in Example 1-2, dispersed in a SC solution, was injected into the microchannel of the PCR chip prepared in Example 4 (1) using a pipette. Then, after injecting a PCR solution into the microchannel and waiting for 30 minutes, a PCR chip 3 was prepared by buffer-exchanging with mineral oil. The composition (v/v) of the PCR solution was 6.25% of templates (β-actin [5'-CCTGGCACCCAGCACAATGAAGATCAAGATCATTGC

TCCTCCTGAGCGCAAGTACTCCGTGTGGATCGGC-3' (SEQ ID NO:

3)]), 43.75% of DI water and 50% of SYBR 1 Mastermix (Nanobiosys).

Figure 6A:
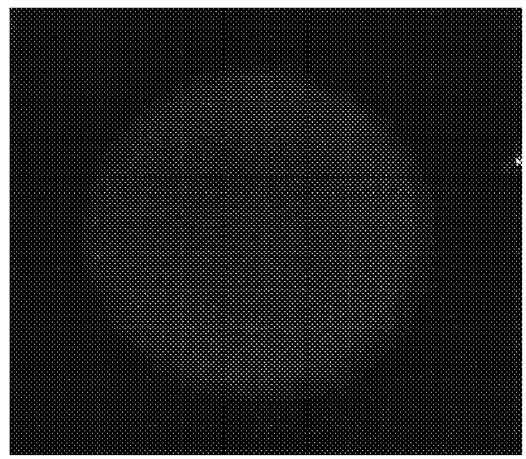
FIG. 6A to FIG. 6D show fluorescence microscopic images showing the result of analyzing nucleic acid amplification using a porous particle composite for PCR according to another exemplary embodiment of the present disclosure.
Figure 6B:
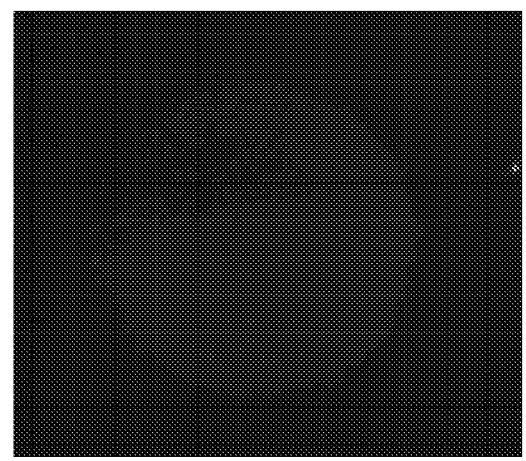
Figure 6C:
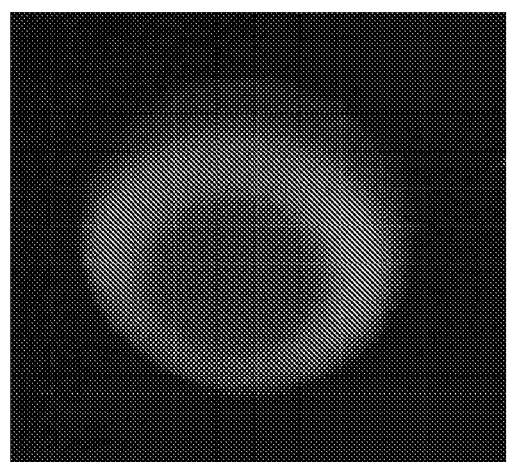
Figure 6D:
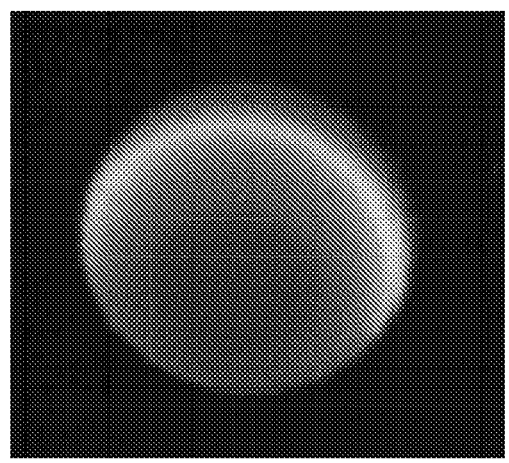
Figure 7:
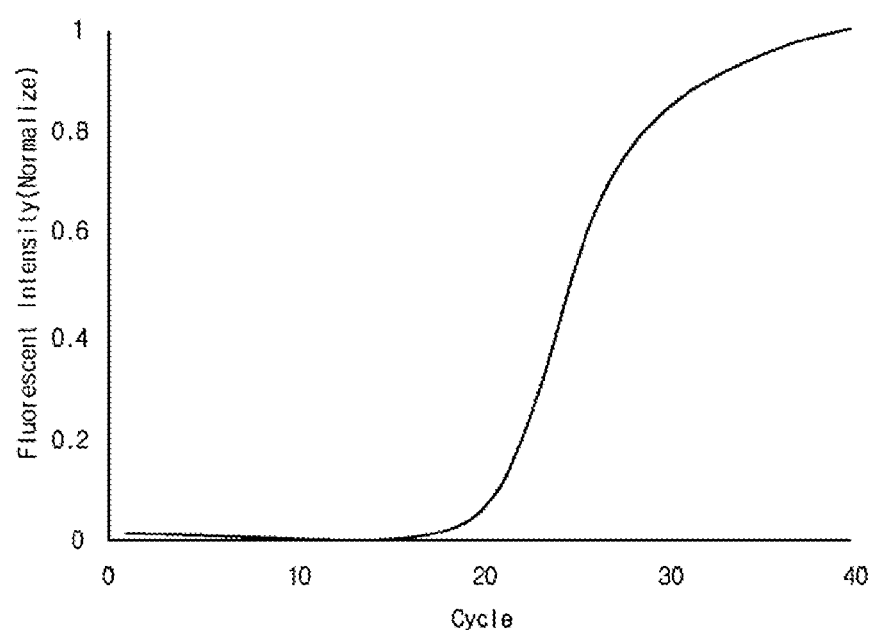
FIG. 7 shows a result of quantifying the result of nucleic acid amplification using a porous particle composite for PCR according to another exemplary embodiment of the present disclosure.

(2) After placing the PCR chip 3 on a fluorescence microscope (Zeiss Axionplan 2 imaging (LSM 5 PASCAl)), polymerase chain reaction was conducted according to the following temperature cycles by irradiating varying light from a light source (2-W, 800-nm laser) 3 mm apart from the PCR chip 3. Pre-denaturation was performed at 95° C. for 8 seconds, denaturation at 95° C. for 4 seconds, and annealing at 60° C. for 20 seconds. The temperature of the porous particle composite was adjusted to 95° C. with a duty of 60%, or the temperature of the porous particle composite was adjusted to 60° C. with a duty of 30%, with the frequency of power supplied to the laser fixed to 1000 Hz. The polymerase chain reaction was conducted for a total of 40 cycles. After each cycle, the fluorescence image of the porous particle composite was obtained and the fluorescence intensity was quantified. FIG. 6A to FIG. 6D show a result of the fluorescence microscopic measurement of the porous particle composite after specific cycles. FIG. 6A is the fluorescence image before cycling, FIG. 6B is the fluorescence image after 10 cycles, FIG. 6C is the fluorescence image after 25 cycles, and FIG. 6D is the fluorescence image after 40 cycles. FIG. 7 shows a result of quantifying the fluorescence intensity of the porous particle composite after each cycle.

(3) From FIGS. 6 and 7, it can be seen that the fluorescence intensity becomes stronger with the progress of cycles. It can be seen that polymerase chain reaction can be conducted through self-heating of the porous particle composite when carbon nanoelements are used.

3. Nucleic Acid Amplification Using Porous Particle Composites Prepared Under Different Conditions (1) A porous particle composite for PCR dispersed in a SC solution was prepared under the same condition as in Example 1-2, except that sonication was not conducted.

(2) After mixing 40% of PEG 600, 20% of PEG 700DA, 35% of the carbon nanoelement solution (0.25 mg of rGO per 1 mL) and 5% (v/v) of Darocur 1173 and preparing a solution by performing vortexing and spinning down, the solution was mixed with 100 µM 3-actin reverse primers

[5'-GCCGATCCACACGGAGTACT-3' (SEQ ID NO: 2)]

and 10 µM β-actin forward primers

[5'-CCTGGCACCCAGCACAAT-3' (SEQ ID NO: 1)]

at a volume ratio of 9:3.5:1. Then, after performing vortexing and spinning down, the solution was cured by irradiating UV. The cured particles were put in a SC solution (DI water+sodium chlorate (sodium chlorate concentration: 0.2 wt %)) and vortexing and spinning down were performed for 20 seconds. After buffer-exchanging with a SC solution and performing vortexing and spinning down for 20 seconds for a total of 6 times, a porous particle composite for PCR dispersed in a SC solution was prepared by buffer-exchanging with a fresh SC solution.

(3) Nucleic acid amplification experiment was conducted under the same condition as in Example 5-2, except that the SC solution in which the porous particle composite prepared in Example 5-3 (1) and (2) was dispersed was used instead of the SC solution in which the porous particle composite prepared in Example 1-2 was dispersed. After a total of 40 cycles, the fluorescence intensity was compared.

(4) As a result of comparing the fluorescence intensity, it was confirmed that the fluorescence intensity was significantly lower when the porous particle composite prepared in Example 5-3 (1) and (2) was used as compared to when the porous particle composite prepared in Example 1-2 was used. It seems that, when the photothermal nanoelements were mixed with the primers but sonication was not performed for a predetermined time, PCR was not conducted sufficiently because the primers were not sufficiently attached to the photothermal nanoelements and that, when both primers were bound to the porous particle network instead of attaching one primer to the photothermal nanoelements, PCR was not conducted sufficiently because both primers were fixed tightly inside the porous particles. That is to say, the primers can be attached to the surface of the photothermal nanoelements through sonication and the primers attached to the photothermal nanoelements are detached from the surface of the photothermal nanoelements due to the heat provided to conduct PCR. Consequently, the decrease in PCR efficiency can be prevented although both primers are located inside the porous particles.

Although various exemplary embodiments of the present disclosure were described, those exemplary embodiments are only examples for embodying the technical idea of the present disclosure and it should be interpreted that all modifications and changes for embodying the technical idea of the present disclosure are comprised within the scope of the present disclosure.

The invention claimed is:

1. A porous particle composite for PCR, comprising porous particles and photothermal nanoelements;
   wherein the porous particles are a hydrophilic polymer in solid state,
   wherein a porosity of the porous particles is 10-95 v/v % and a particle diameter of the porous particles is 10 µm to 1 mm;
   wherein the photothermal nanoelements have a diameter or length of 1-500 nm and are fixed to the porous particles;
   wherein when exposed to light having a wavelength of 800 nm the photothermal nanoelements absorb the light and generate heat; and
   wherein the photothermal nanoelements are not rod-shaped.

2. The porous particle composite for PCR according to claim 1, wherein the photothermal nanoelement is any one or more selected from a group consisting of a metal nanoparticle, a carbon nanoelement, an inorganic nanoelement, an organic nanoelement, a quantum dot and a rare-earth element;
   wherein the carbon nanoelement is not a carbon nanotube.

3. The porous particle composite for PCR according to claim 2, wherein 0.25-50 mg of the photothermal nanoelements are present in 1 mL of the porous particles.

4. The porous particle composite for PCR according to claim 3, wherein the photothermal nanoelements are physically or chemically fixed to the porous particles.

5. The porous particle composite for PCR according to claim 4, wherein one primer of a forward primer and a reverse primer is fixed inside the porous particles, the other primer is physically or chemically attached to the surface of the photothermal nanoelements fixed inside the porous particles, and the other primer is detached from the photothermal nanoelements due to heat generated in the photothermal nanoelements when light is irradiated to the porous particle composite for PCR.

6. A method for preparing the porous particle composite for PCR according to claim 1, the method comprising: a binding step of, by mixing one primer of a forward primer and a reverse primer in a solution wherein photothermal nanoelements are dispersed, binding the one primer onto the surface of the photothermal nanoelements; a first mixing step of forming a first mixture solution by mixing the photothermal nanoelements with the one primer bound and a porous particle-forming polymer solution; a second mixing step of forming a second mixture solution by mixing the first mixture solution with the other primer; and a curing step of preparing a porous particle composite having porosity, having the other primer of target nucleic acids fixed to inner pores and having the photothermal nanoelements with the one primer attached fixed to the inner pores by curing the second mixture solution.

7. The method for preparing a porous particle composite for PCR according to claim 6, wherein the binding step is performed by mixing one primer of a forward primer and a reverse primer in a solution wherein photothermal nanoelements are dispersed and conducting sonication for 30-60 minutes.

8. A nucleic acid amplification device comprising a PCR chip comprising a porous particle composite which amplifies target nucleic acids by polymerase chain reaction inside thereof, a light irradiation unit which irradiates light to the porous particle composite and a controller which adjusts the light irradiated by the light irradiation unit such that the porous particle composite has a temperature where polymerase chain reaction occurs, wherein the porous particle composite is the porous particle composite according to claim 1.

9. The nucleic acid amplification device according to claim 8, wherein the intensity of the light irradiated by the light irradiation unit is controlled by controlling any one or more of the current, voltage, duty cycle and frequency of power applied to the light irradiation unit.

10. The nucleic acid amplification device according to claim 8, wherein the controller comprises a light setting unit which sets the condition of the light irradiated by the light irradiation unit such that the porous particle composite has a temperature where polymerase chain reaction occurs.

11. The nucleic acid amplification device according to claim 8, wherein the nucleic acid amplification device further comprises a measurement unit which measures the porous particle composite located in the PCR chip to which light has been irradiated by the light irradiation unit and the controller comprises a result analysis unit which determines the presence or amount of target nucleic acids by analyzing the result measured by the measurement unit.

12. A nucleic acid amplification method comprising a sample reaction step of reacting a porous particle composite which amplifies target nucleic acids by polymerase chain reaction inside thereof with a sample, a light irradiation step of irradiating light to the porous particle composite which has reacted with the sample such that the porous particle composite has a temperature where polymerase chain reaction occurs after the sample reaction step, a measurement step of measuring the change of the porous particle composite after the light irradiation step and an analysis step of determining the presence or amount of target nucleic acids by analyzing the result measured in the measurement step, wherein the porous particle composite is the porous particle composite according to claim 1.

13. The porous composite for PCR according to claim 5 wherein the other primer is chemically attached to the surface of the photothermal nanoelements by a linker having a length of 1-100 nm.

* * * * *

SEQUENCE LISTING

<160> NUMBER OF SEQ ID NOS: 3

<210> SEQ ID NO 1
<211> LENGTH: 18

```
<212> TYPE: DNA
<213> ORGANISM: Artificial Sequence
<220> FEATURE:
<223> OTHER INFORMATION: beta-actin forward primer

<400> SEQUENCE: 1
cctggcaccc agcacaat                                                       18

<210> SEQ ID NO 2
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 2
gccgatccac acggagtact                                                     20

<210> SEQ ID NO 3
<211> LENGTH: 70
<212> TYPE: DNA
<213> ORGANISM: Artificial Sequence
<220> FEATURE:
<223> OTHER INFORMATION: beta-actin

<400> SEQUENCE: 3
cctggcaccc agcacaatga agatcaagat cattgctcct cctgagcgca agtactccgt         60
gtggatcggc                                                                70
```